(12) United States Patent
Katakowski

(10) Patent No.: US 11,667,879 B2
(45) Date of Patent: Jun. 6, 2023

(54) DYNAMIC INCUBATOR SYSTEM AND METHOD

(71) Applicant: FOREVER LABS, INC., Ann Arbor, MI (US)

(72) Inventor: Mark Katakowski, Ann Arbor, MI (US)

(73) Assignee: FOREVER LABS, INC., Ann Arbor, MI (US)

( * ) Notice: Subject to any disclaimer, the term of this patent is extended or adjusted under 35 U.S.C. 154(b) by 177 days.

(21) Appl. No.: 16/814,696

(22) Filed: Mar. 10, 2020

(65) Prior Publication Data

US 2020/0291345 A1    Sep. 17, 2020

Related U.S. Application Data

(60) Provisional application No. 62/816,624, filed on Mar. 11, 2019.

(51) Int. Cl.
*C12M 3/00* (2006.01)
*C12M 1/00* (2006.01)
(Continued)

(52) U.S. Cl.
CPC ............ *C12M 41/14* (2013.01); *C12M 23/44* (2013.01); *C12M 41/16* (2013.01); *C12M 41/34* (2013.01);
(Continued)

(58) Field of Classification Search
CPC ...... C12M 23/24; C12M 23/44; C12M 41/14; C12M 41/16; C12M 41/22; C12M 41/34; C12M 41/44; C12M 41/46; C12M 41/48
See application file for complete search history.

(56) References Cited

U.S. PATENT DOCUMENTS 5,985,653 A    11/1999  Armstrong et al.
6,008,010 A    12/1999  Greenberger et al.
(Continued)

FOREIGN PATENT DOCUMENTS

CN    108587906 A    9/2018
EP    2692851 A2    2/2014
(Continued)

OTHER PUBLICATIONS

International Preliminary Report on Patentability, corresponding international application No. PCT/US2020/021789, dated Aug. 25, 2021.
(Continued)

*Primary Examiner* — Lydia Edwards
(74) *Attorney, Agent, or Firm* — Marshall, Gerstein & Borun LLP

(57) ABSTRACT

A dynamic incubator system and method for mammalian cells. The dynamic incubator system includes an incubator and a programming device communicatively coupled to the incubator. The programming device includes a memory, one or more processors, a display, and an input mechanism. The programming device is adapted to enable at least one preset temperature and gas concentration sequence to be one or more of designed for the interior of the incubator, saved to the memory of the programming device and/or selected for implementation within the interior of the incubator. The at least one temperature and gas concentration sequence includes programmed changes to the temperature and a $CO_2$ gas concentration. A purging mechanism is coupled to the incubator and releases a portion of a gas concentration to enable rapid changes in the temperature and gas concentration in the incubator.

15 Claims, 11 Drawing Sheets

(51) Int. Cl.
*C12M 1/34* (2006.01)
*C12M 1/36* (2006.01)

(52) U.S. Cl.
CPC ............ *C12M 41/44* (2013.01); *C12M 41/46* (2013.01); *C12M 41/48* (2013.01)

(56) References Cited

U.S. PATENT DOCUMENTS

| | | |
|---|---|---|
| 6,835,353 B2 | 12/2004 | Smith et al. |
| 7,045,349 B2 | 5/2006 | Benedict et al. |
| 7,332,158 B2 | 2/2008 | Yang |
| 9,206,383 B2 | 12/2015 | Vunjak-Novakovic et al. |
| 9,623,051 B2 | 4/2017 | Leach et al. |
| 2003/0109037 A1 | 6/2003 | Reid et al. |
| 2011/0034975 A1 | 2/2011 | Ferree |
| 2017/0081638 A1 | 3/2017 | Ma |
| 2018/0066223 A1* | 3/2018 | Lim ................ C12M 41/48 |

FOREIGN PATENT DOCUMENTS

| | | |
|---|---|---|
| FR | 2849862 A1 | 7/2004 |
| WO | WO-2005/093038 A1 | 10/2005 |

OTHER PUBLICATIONS

International Search Report and Written Opinion, corresponding international application No. PCT/US2020/021789, dated Jun. 22, 2020.
Reissis et al., The Effect of Temperature on the Viability of Human Mesenchymal Stem Cells, Journal List, Stem Cell Res Ther 2013 4(6): 139, Published online Nov. 15, 2013.
Caldwell et al., Immunogenic Potential of Human Bone Marrow Mesenchymal Stromal Cells is Enhanced by Hyperthermia, Cytotherapy. Dec. 2018;20(12):1437-1444. doi: 10.1016/j.jcyt.2018.10.002. Epub Oct. 31, 2018.
Lambertini et al., Hypoxia Preconditioning of Human MSCs: a Direct Evidence of HIF-1α and Collagen Type XV Correlation, Cell Physiol Biochem. 2018;51(5):2237-2249. doi: 10.1159/000495869. Epub Dec. 7, 2018.

* cited by examiner

DYNAMIC INCUBATOR SYSTEM AND METHOD

CROSS REFERENCE TO RELATED APPLICATIONS

This application claims the benefit of U.S. Provisional Application No. 62/816,624 filed Mar. 11, 2019. The entire contents of this application are incorporated herein by reference in their entirety.

TECHNICAL FIELD

This disclosure relates to cell incubator systems and methods, and in particular, to a system and method for dynamically incubating cells, such as eukaryotic cells or mammalian cells.

BACKGROUND

Mammalian cells are typically grown under carefully controlled conditions. These conditions vary by cell type, but generally consist of a suitable flask or dish, with a substrate or medium that supplies essential nutrients (amino acids, carbohydrates, vitamins, minerals), growth factors, hormones, and regulates pH, osmotic pressure, and temperature. Cells are grown and maintained at an appropriate temperature and gas mixture (typically, 37° C., 5% $CO_2$ for mammalian cells) in a cell incubator. Commercially available cell incubators are designed to keep cells at a constant temperature and gas mixture.

It is generally known that when culturing mesenchymal stem cells, and other mammalian cells, some cellular processes are altered by changes in temperature, and changes in both $O_2$ and/or $CO_2$ concentration. Indeed, it has been reported that increased temperature can alter the secretome of mesenchymal stem cells (https://www.ncbi.nlm.nih.gov/pubmed/30389270) and that hypoxia improves mesenchymal stem cell osteopotency (https://www.ncbi.nlm.nih.gov/pubmed/30537732).

It is also generally known that cells within the human body do not remain at a constant temperature, experience variable concentrations of $O_2$ and $CO_2$, and are subjected to physiological stresses. Not only do these stresses alter signaling mechanisms in cells, but populations of cells take advantage of these stressors to improve the overall health and viability of the cell population. That is, after exposing cells to changes in temperature and/or gas concentrations, the resulting population of cells are healthier and more viable. However, standard incubators enable different settings in temperature or gas concentrations, but they do not enable programmable rapid changes in these conditions. Standard incubators have a significant deficiency in that they do not enable the design, control, and implementation of dynamic temperature and gas concentrations (and consequently pH variations) over time, and thus maintain mammalian cells in conditions distinct from in vivo physiological conditions, which are not steady-state. Indeed, constant temperature and gas concentrations in standard mammalian cell incubation disregards the possibility that natural mammalian cellular function requires dynamic changes in temperature and gas concentrations, and that cellular health and physiologically germane cellular dynamics rely upon intermittent changes in temperature and gas concentrations.

SUMMARY OF THE DISCLOSURE

In accordance with one exemplary aspect of the present disclosure, a dynamic incubator system for cells, such as mammalian cells, comprises an incubator having a housing with an interior adapted to contain mammalian cells and a display for providing one or more of an actual temperature and a gas concentration of the interior of the incubator. A programming device is communicatively coupled to the incubator via a communication network. The programming device includes a memory, one or more processors, a display, and an input mechanism. The programming device is also adapted to enable at least one preset temperature and gas concentration sequence to be one or more of designed for the interior of the incubator, saved to the memory of the programming device and/or selected for implementation within the interior of the incubator. The at least one temperature and gas concentration sequence includes programmed changes to the temperature and one or more of a $CO_2$ gas concentration or an $O_2$ gas concentration in the interior of the incubator. In addition, a purging mechanism is coupled to the incubator and the programming device. The purging mechanism is adapted to release one or more of: (1) a portion of a gas concentration disposed within the interior of the incubator; or (2) an amount of water disposed in an internal tank of the incubator or a water jacket disposed on the incubator to enable rapid changes in the temperature and one or more of gas concentration in the interior of the incubator or the amount of water in the internal tank or the water jacket.

In accordance with another exemplary aspect of the present disclosure, a method of dynamically incubating cells, such as mammalian cells, comprises one of designing or selecting at least one temperature and gas concentration sequence for an interior of an incubator via a programming device communicatively coupled to the incubator. The method further comprises executing the at least one temperature and gas concentration sequence within the interior of the incubator. The at least one temperature and gas concentration includes programmed changes to the temperature and one or more of an $CO_2$ gas concentration or an $O_2$ gas concentration in the interior of the incubator after designated periods of time. Lastly, the method further includes enabling rapid changes in temperature and gas concentrations within the interior of the incubator via a purging mechanism coupled to the incubator and the programming device.

Additional optional aspects and features are disclosed, which may be arranged in any functionally appropriate manner, either alone or in any functionally viable combination, consistent with the teachings of the disclosure. Other aspects and advantages will become apparent upon consideration of the following detailed description.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings are necessarily to scale.

DETAILED DESCRIPTION

Generally, a system and method of dynamically incubating cells, such as mammalian cells, is disclosed. Specifically, in vitro cell expansion can be greatly improved by adding dynamic changes in temperature, gas concentrations, and/or mechanical stress to the incubation system. A dynamic incubation system includes an incubator and a programming device communicatively coupled to the incubator. The programming device enables changes in temperature and gas concentrations (e.g., $CO_2$ and $O_2$) to be preprogrammed, such as having at least one preset temperature and gas concentration sequence designed and/or saved via the programming device, allowing cells to be grown in dynamic conditions. In addition, a purging mechanism, such as an air pump with an air lock, is also communicatively coupled to both the incubator and the programming device. The purging mechanism releases a portion of the gas concentration within the incubator to enable rapid changes in the temperature and gas concentrations within the incubator, as explained more below. So configured, growing mammalian cells in such dynamic temperature and gas concentrations according to specific sequences results in reduced cell doubling time, reduced cellular senescence, and reduced inflammatory cytokine production when compared to cells grown at constant temperature and gas concentrations.

Figure 1A:
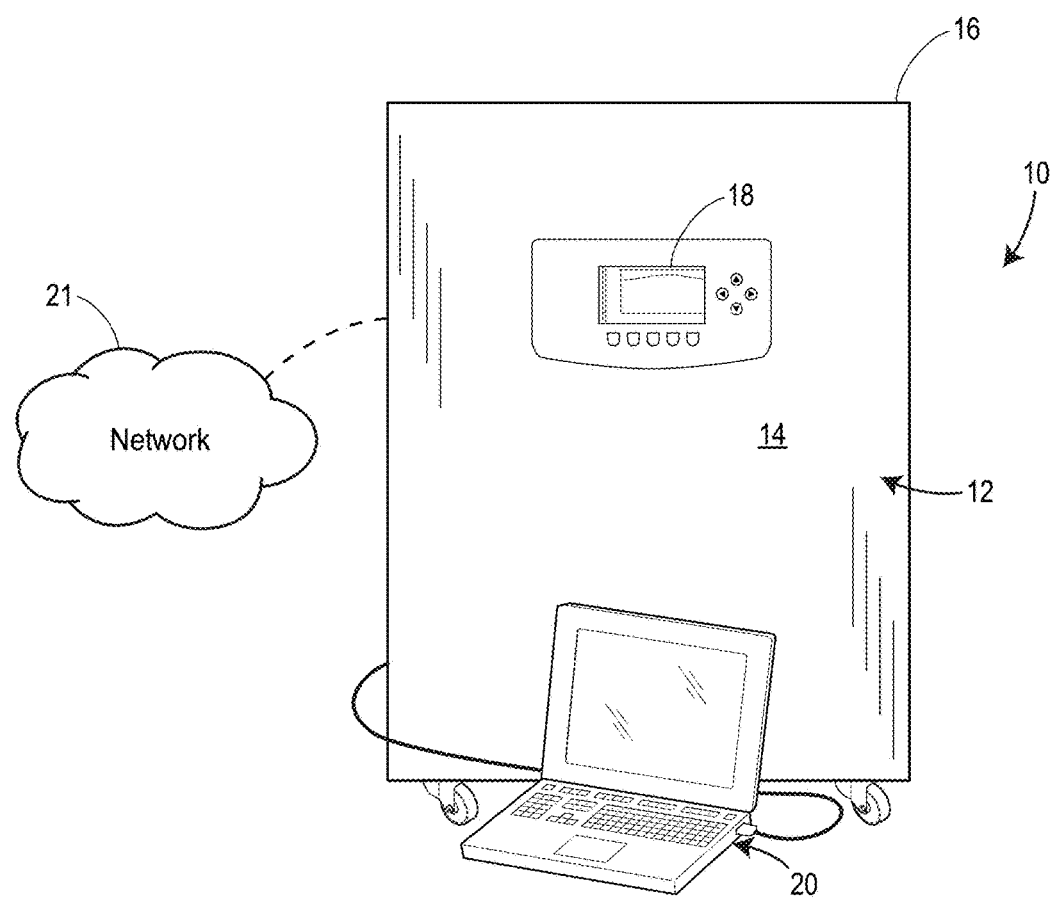
FIG. 1A is front perspective view of a dynamic incubator system according to one aspect of the present disclosure.
Figure 1B:
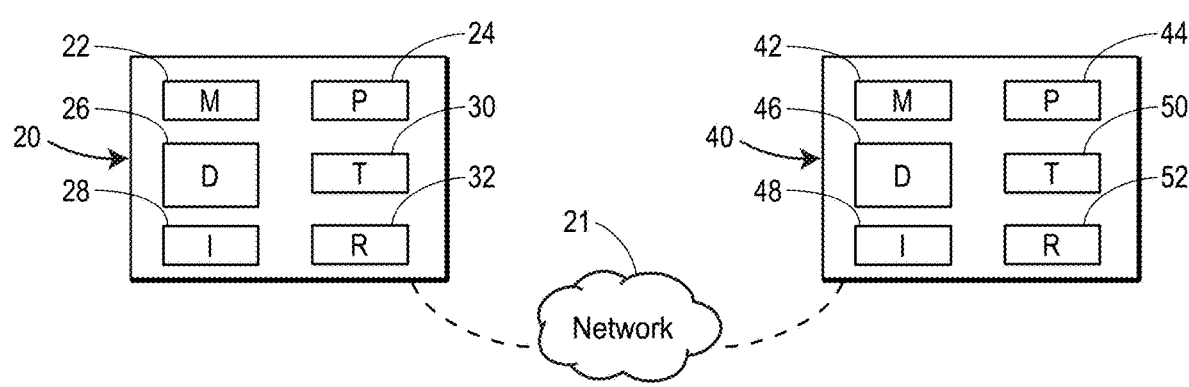
FIG. 1B is a block diagram of a portion of the dynamic incubator system of FIG. 1A.

Referring now to FIGS. 1A and 1B, a dynamic incubator system 10 according to the present disclosure is depicted. The dynamic incubator system 10 includes an incubator 12 having a housing 14 with an interior 16 adapted to contain stem cells. A display 18 is disposed on an outside portion of the housing 14 of the incubator 12, such as a central, front outside portion of the housing 14, as depicted in FIG. 1. Alternatively, the display 18 may be disposed on any other outside portion of the housing 14 of the incubator 12 and still fall within the scope of the present disclosure. The display 18 provides one or more of an actual temperature of the interior 16 of the incubator 12 or an actual gas concentration, such as one or more of a $CO_2$ gas concentration and an $O_2$ gas concentration, of the interior 16 of the incubator 12.

A programming device 20 is communicatively coupled to the incubator 12 via communication network 21. As will be appreciated, the communication network 21 may be one of a wired or a wireless connection and fall within the scope of the present disclosure. As depicted in FIG. 1B, the programming device 20 includes a memory 22, one or more processors 24, a display 26, an input mechanism 28, at least one transmitter 30, and at least one receiver 32. The programming device 20 is adapted to enable at least one temperature and gas concentration sequence to be designed and preprogrammed for the interior 16 of the incubator 12 via the input mechanism 28, for example. Alternatively and/or additionally, the programming device 20 may be incorporated into the incubator housing 14 itself using the incubator display mechanism 18 and input mechanism. Alternatively and/or additionally, the programming device 20 may also enable at least one preset temperature and gas concentration sequence to be saved to the memory 22 of the programming device 20. In this manner, the at least one preset temperature and gas concentration sequence may be displayed on the display 26, for example, and selected for implementation within the interior 16 of the incubator 12 via one or more of the display 26 or the input mechanism 28, as explained more below.

In addition, the at least one temperature and gas concentration sequence includes programmed changes to the temperature and a $CO_2$ gas concentration in the interior 16 of the incubator 12. In another example, the at least one temperature and gas concentration sequence may include programmed changes to the temperature, a $CO_2$ gas concentration, and an $O_2$ gas concentration in the interior 16 of the incubator 12, as also explained more below.

As further depicted in FIG. 1B, the dynamic incubator system 10 may further include a user control device 40. The user control device 40 may be communicatively coupled to at least one of the programming device 20 and the communication network 21 and used to activate the programming device 20, for example. In addition, the user control device 40 includes a memory 42 and one or more processors 44. Further, the user control device 40 may also include a display 40, an input 42, at least one transmitter 50, and at least one receiver 52. So configured, a user may remotely activate the programming device 20 via the user control device 40 to control the temperature and gas concentration conditions within the interior 16 of the incubator 12.

Moreover, the programming device 20 may include a personal computer, such as a laptop computer, as depicted in FIG. 1A. However, as will be appreciated, the programming device 20 may take the form of various other electronic devices capable of the implementing the same functions as the personal computer and still fall within the scope of the present disclosure. For example, the programming device 20 may alternatively and/or additionally include any one or more of a smart phone, a tablet, an e-reader or any other similar electronic device, or the programming device 20 may be incorporated into the incubator 12 itself.

Figure 2A:
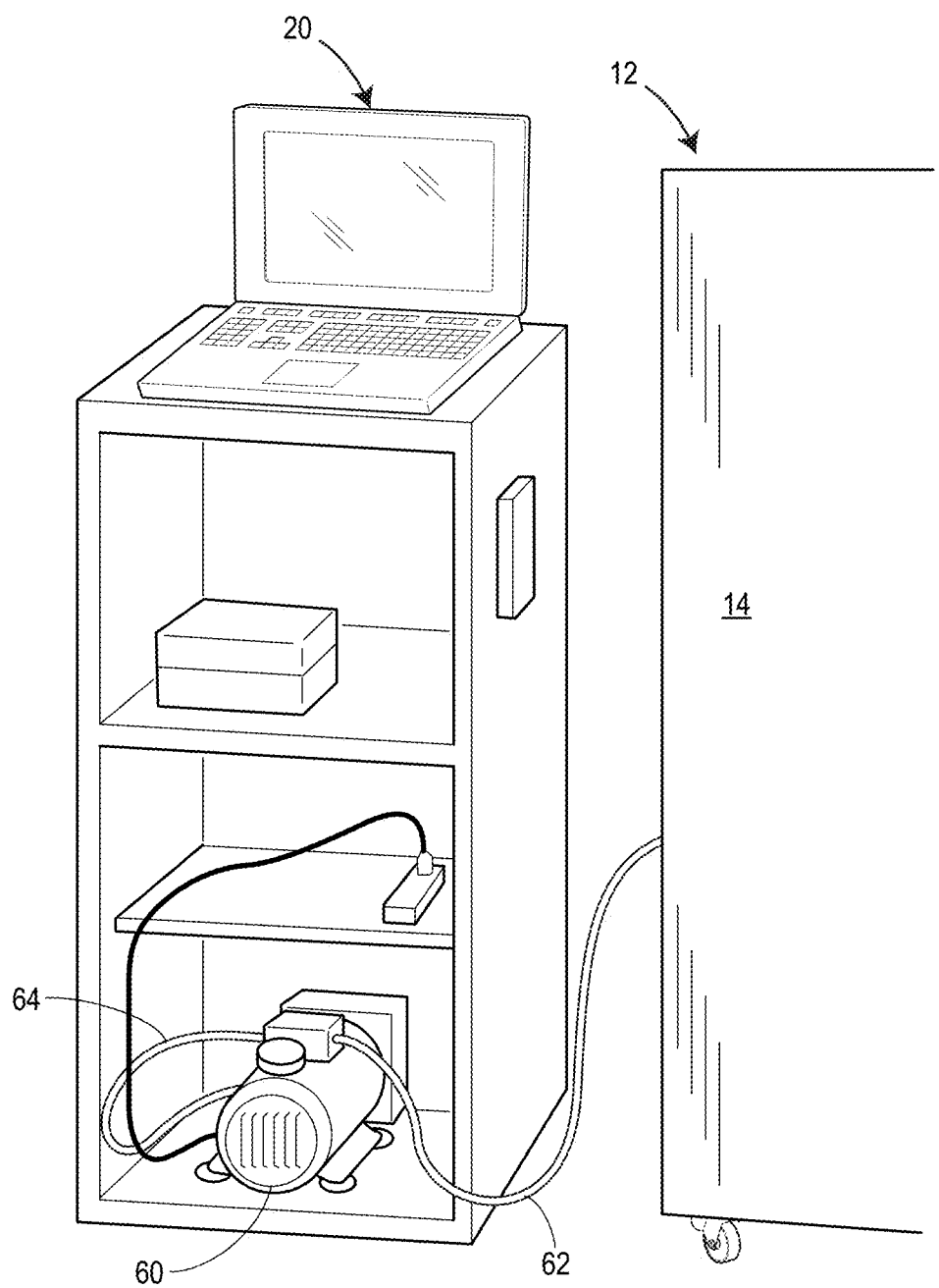
FIG. 2A is another front perspective view of the dynamic incubator system of FIG. 1A, with a purging mechanism according to one aspect of the present disclosure.

Referring now to FIG. 2A, the dynamic incubator system 10 further includes a purging mechanism 60. In some examples, the purging mechanism is a pump, such as an air pump. However, the purging mechanism 60 may alternatively and/or additionally take the form of various other devices and/or machines capable of implementing the functions of the purging mechanism 60 described in more detail below and still fall within the scope of the present disclosure. In FIG. 2A, the purging mechanism 60 includes an air pump having an air inlet tube 62 and an air outlet tube 64. As further depicted, the purging mechanism 60 is also communicatively coupled to the programming device 20 via a communication network, such as the communication network 21, which may be one or more of a wired connection or a wireless connection. The purging mechanism 60 and the coupled programming device 20 may be contained within the housing 14 of the incubator 12.

Figure 2B:
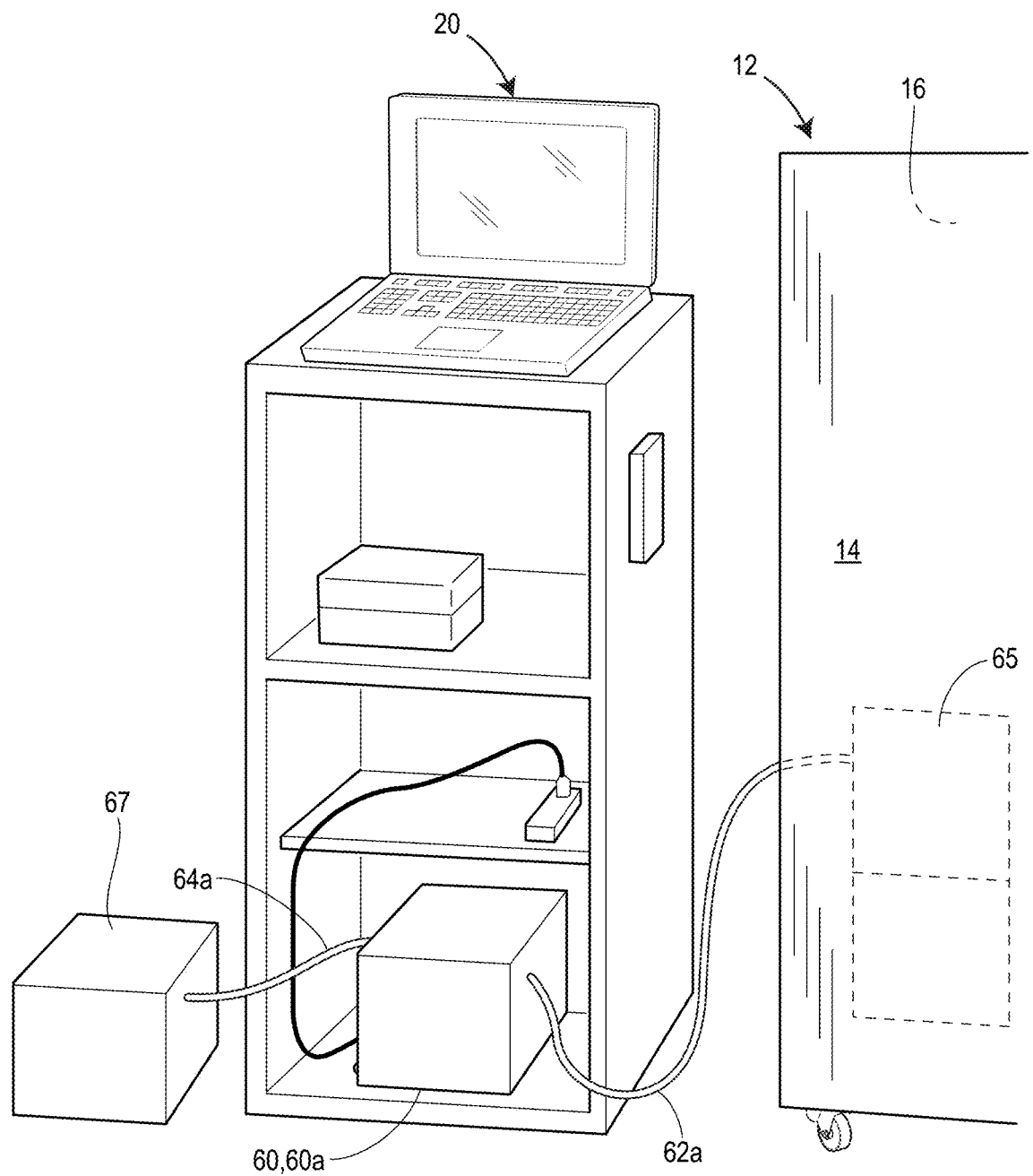
FIG. 2B is a front perspective view of the dynamic incubator system of FIG. 2A including another purging mechanism according to another aspect of the present disclosure.

Referring now to FIG. 2B, another purging mechanism 60 that may alternatively or additionally be used with the dynamic incubator system 10 is depicted. In this example, the purging mechanism 60 is a water pump 60*a* that cycles water from an internal water tank 65, disposed within the interior 16 of the incubator 12, to an external water tank 67 and includes a water inlet tube 62*a* and a water outlet tube 64*a*. Specifically, the water inlet tube 62*a* is coupled to the internal water tank 65, and the water outlet tube 64*a* is coupled to the external water tank 67. The water pump 60*a* may more efficiently change the temperature of the interior 16 of the incubator 12. In one example, the external water tank 67 may heat or cool the water to better function as a heat source or heat sink, respectively, when the water from the water pump 60*a* is introduced into the internal water tank 65 in the interior 16 of the incubator 12.

Figure 2C:
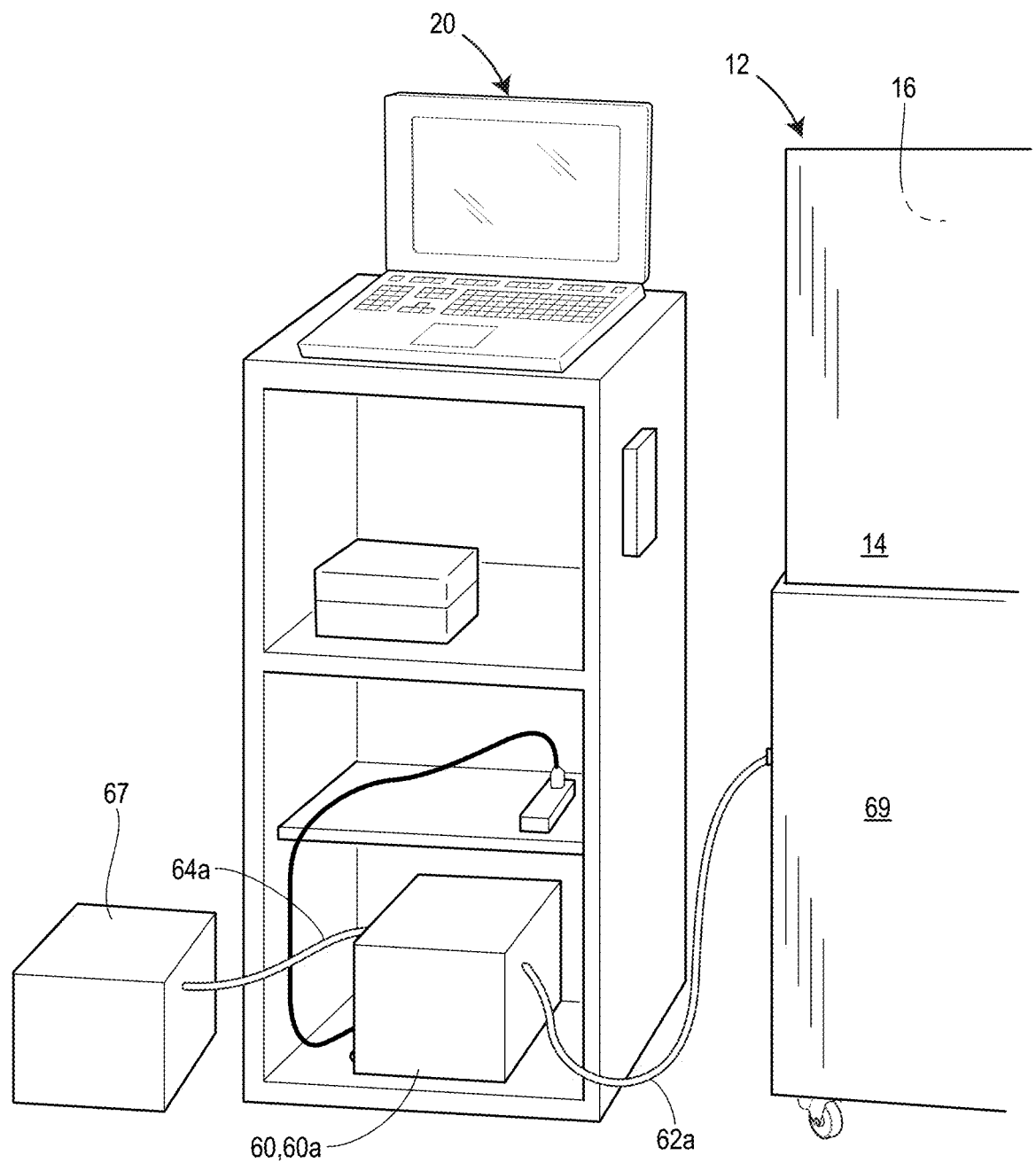
FIG. 2C is a front perspective view of the dynamic incubator system of FIG. 2B according to another aspect of the present disclosure.

In another example, and instead of the internal water tank 65 disposed within the incubator 12, the water pump 60*a* may exchange water from the external water tank 67 into a water jacket 69. The water jacket 69 surrounds the interior 16 of the incubator 12 and is disposed on an outside area of the housing 14, as depicted in FIG. 2C. In this example, the water jacket 69 extends around at least a part of the interior 16 of the incubator 12 and upwardly extends to an approximate mid-way portion and/or center area of the housing 14 of the incubator 12. However, it will be appreciated that the water jacket 69 may extend up to a top area of the housing 14 and/or extend to any other point or area along the length of the housing 14 of the incubator 12 and still fall within the scope of the present disclosure.

Alternatively, both the water pump 60*a* and the water jacket 69 may more generally be a fluid pump 60*a* and a fluid jacket 69, each of which uses a heat transfer liquid other than water. For example, any other fluid aside from water, such as oil, synthetic hydrocarbon, silicon based fluids, molten salts, molten metals, and various gases including water vapor, nitrogen, argon, helium and hydrogen, may alternatively be used (instead of water) and still fall within the scope of the present disclosure.

Figure 3:
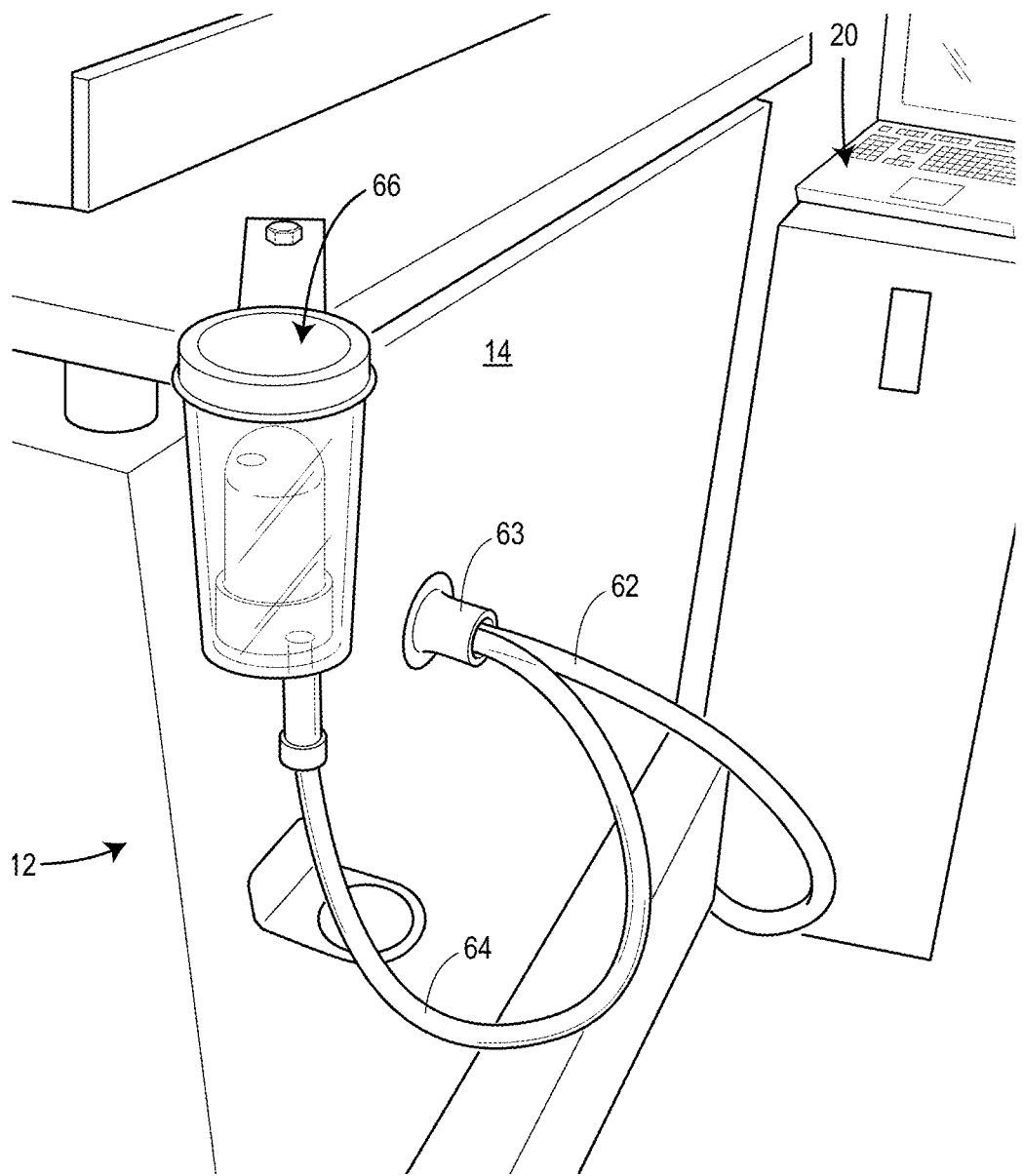
FIG. 3 is a rear perspective view of the dynamic incubator system of FIG. 1A.

Referring now to FIG. 3, a rear view of the dynamic incubator system 10 is depicted. A rear portion of the housing 14 is depicted and includes a port 63. The air inlet tube 62 and the air outlet tube 64 of the purging mechanism 60 are both coupled to the port 63 on the housing 14 of the incubator 12. In addition, the outlet tube 64 is further connected to an air lock assembly 66. The air lock assembly 66 prevents loss of a portion or some of the gas concentration in the interior 16 of the incubator 12 when the purging mechanism 60 is not operating, for example. In some embodiments, the air lock assembly 66, the air inlet tube 62 and the air outlet tube 64 of the purging mechanism 60 may be incorporated in the housing 14 of the incubator 12.

The dynamic incubator system 10 may further include a module stored in the memory 22 of the programming device 60. The module is executable by the at least one processor 24 of the programming device 60 to set a first temperature T1 of the interior 16 of the incubator 12, set a first $CO_2$ gas concentration of the interior 16 of the incubator 12 to a value G1, and then maintain the temperature T1 and the $CO_2$ gas concentration at the value G1 for a time t1. The module may then further set a second temperature T2 of the interior 16 of the incubator 12 and set a $CO_2$ gas concentration of the interior 16 of the incubator 12 to a value G2. The module may then operate the purging mechanism 60 for a time tp to purge a portion of the gas concentration of the interior 16 of the incubator 12. Lastly, the module maintains the second temperature T2 and $CO_2$ gas concentration at the value G2 for a time t3.

In one example temperature and gas concentration sequence, the temperature T1 is 37 degrees C., the $CO_2$ gas concentration value G1 is 5% $CO_2$, the time t1 is about 8 hours, the temperature T2 is 38 degrees C., the $CO_2$ gas concentration value G2 is 5.5% $CO_2$, the time tp is about 1 minute, and the time t2 is about 30 minutes.

In another example temperature and gas concentration sequence, the temperature T1 is 38 degrees C., the $CO_2$ gas concentration value G1 is 6% $CO_2$, the time t1 is about 60 minutes, the temperature T2 is 37 degrees C., the $CO_2$ gas concentration value G2 is 5% $CO_2$, the time tp is about 1 minute, and the time t2 is about 8 hours.

In yet another example temperature and gas concentration sequence, the first temperature T1 is 36 degrees C., the first $CO_2$ gas concentration value G1 is 5.5% $CO_2$, the time t1 is about 120 minutes, the second temperature T2 is 37 degrees C., the second $CO_2$ gas concentration value G2 is 5% $CO_2$, the time tp is about 1 minute, and the time t2 is about 20 hours.

In this example, the module of the programming device 20 is further executable by the processor 24 to: set a $O_2$ gas concentration level to a value G3 after the first temperature T1 and the first $CO_2$ gas concentration value G1 are set, and maintain each of the first temperature T1, the second $CO_2$ gas concentration value G1, and the $O_2$ gas concentration value G3 for the time t1. In addition, the module then sets the $CO_2$ gas concentration value to a value G4 and the $O_2$ gas concentration value to a value G5, and then maintains the $CO_2$ gas concentration value to a value G4 and the $O_2$ gas concentration value to a value G5 for a period of time t1. Still further, the module of the programming device 20 is further executable by the processor 24 to set the $O_2$ gas concentration value to a value zero before the purging mechanism is operated for a time tp. In this example, the at least one or more of the $O_2$ gas concentration value G3 is 18% $O_2$, the $CO_2$ gas concentration value G4 is 6% $CO_2$, and the $O_2$ gas concentration value G5 is 15% $O_2$.

While several example temperature and gas concentration sequences are provided above, it will be understood that various other temperature and gas concentration sequences may alternatively be designed and/or implemented and still fall within the scope of the present disclosure. For example, one or more of the example temperatures T1, T2 and the example gas concentrations G1, G2, G3, G4, and G5 may be many other values. In one example, the temperature values T1 and T2 may change, while the gas concentration values G1-G5 remain the same. In another example, any one of the gas concentration values G1-G5 may change and be different from one the examples provided above, while the temperature values T1 and T2 remain the same. Further, both the temperature values T1 and T2 may change and any one of the gas concentration values G1-G5 may likewise change and still affect dynamic incubation of the cells. Any of such variations still fall within the scope of the present disclosure.

Figure 4:
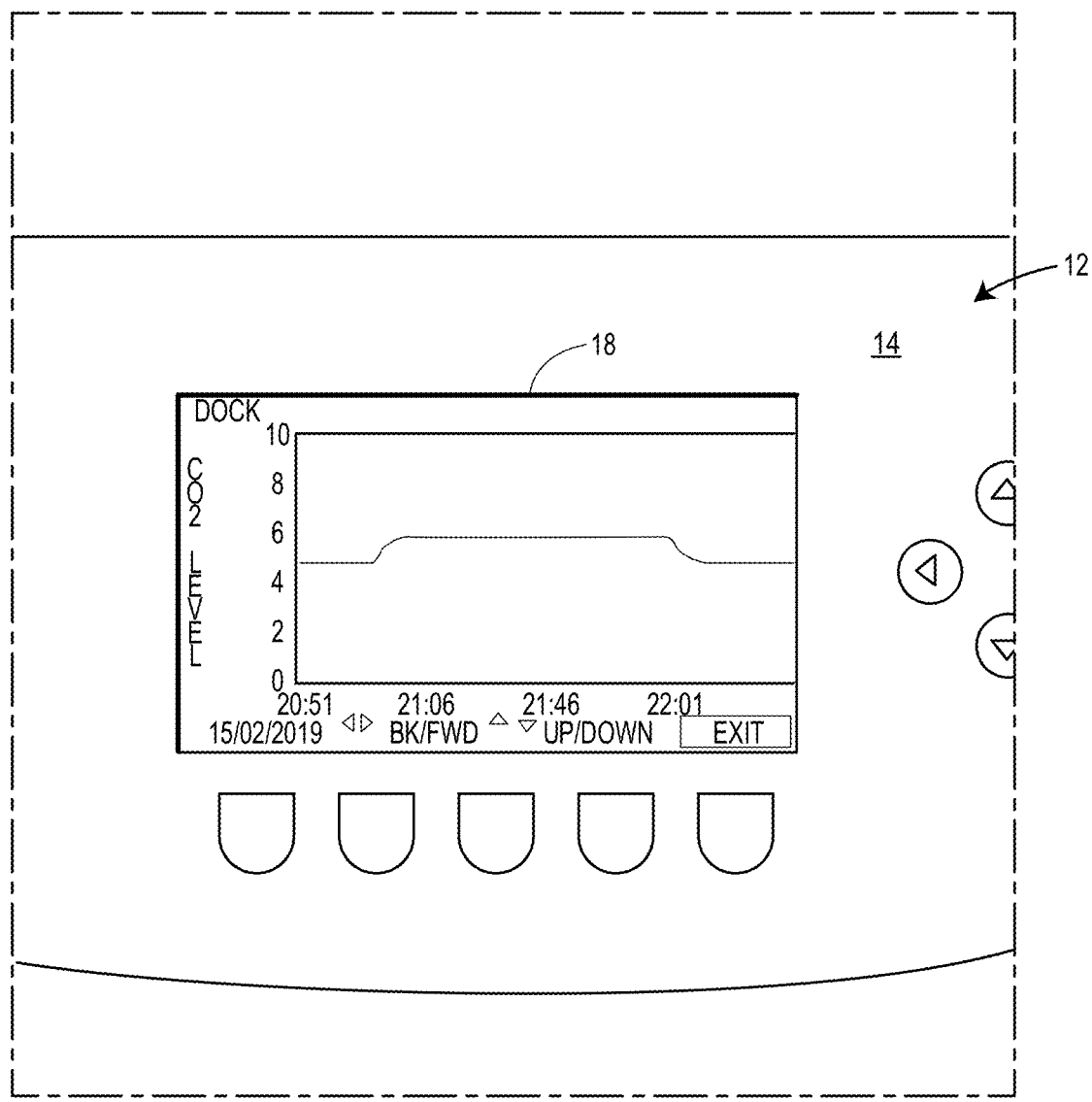
FIG. 4 is a close-up view of a portion of the dynamic incubatory system of FIG. 1A.

Referring now to FIG. 4, a close-up view of the display 18 disposed on the housing 14 of the incubator 12 is depicted. In this example, an actual gas concentration of a $CO_2$ gas concentration disposed within the interior 16 of the incubator 12 over a period of time is displayed. Alternatively and/or additionally, the display 18 may provide an actual temperature within the interior 16 of the incubator over a period of time. Further, the display 18 may also list and/or display at least one log of a previous actual temperature and a previous actual gas concentration over a period of time. Said another way, listings of previous actual temperature and gas concentration ranges and/or sequences may be displayed on the display 18 of the dynamic incubator 12.

Figure 5:
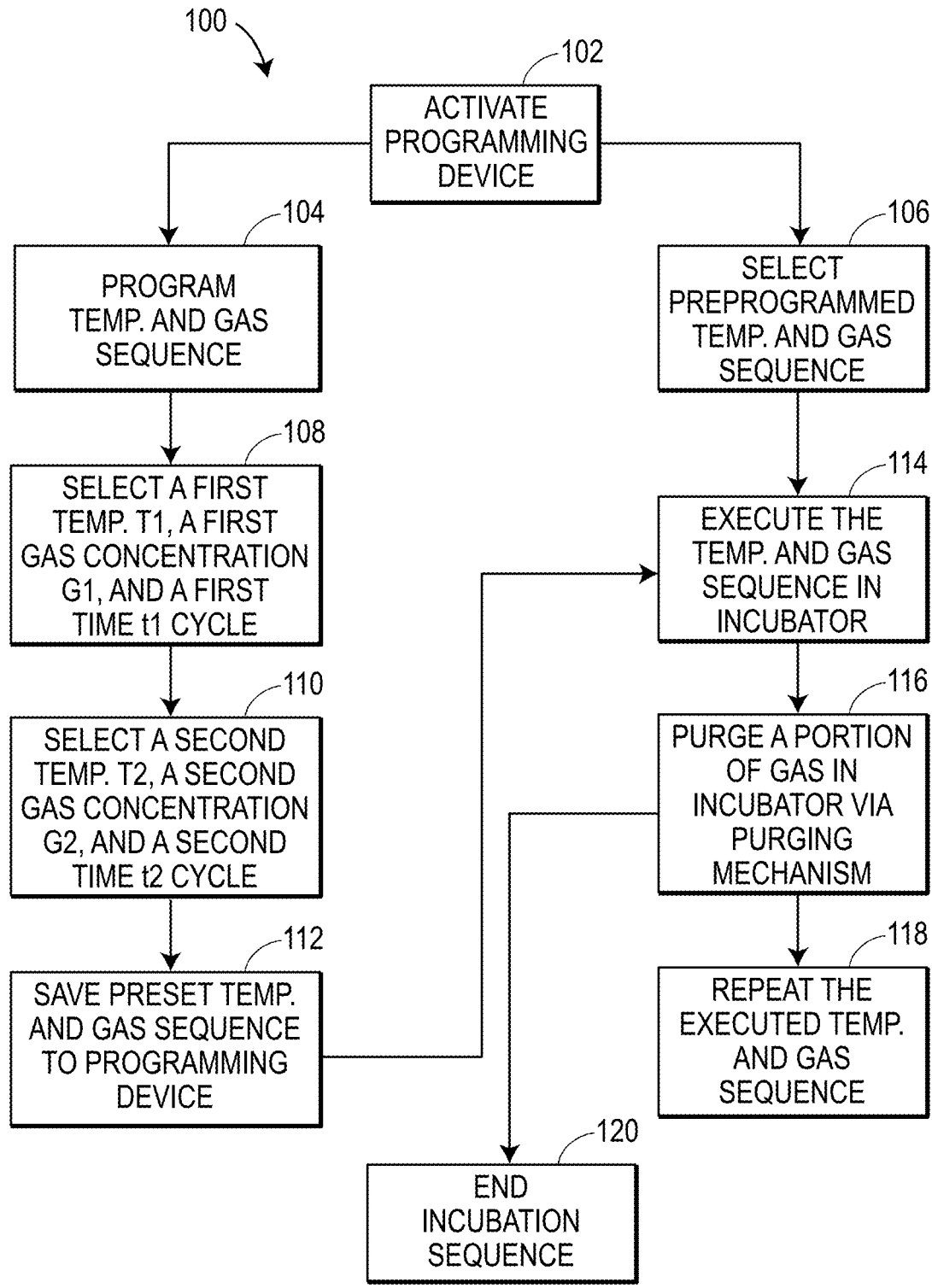
FIG. 5 is an exemplary flow chart depicting a method of one aspect of the present disclosure.

Referring now to FIG. 5, a flowchart of an example method of dynamically incubating stem cells 100 is depicted. The method 100 may be implemented, in whole or in part, on one or more devices or systems such as those shown in the dynamic incubator system 10 of FIGS. 1-4. The method 100 may be saved as a set of instructions, routines, programs or modules on a memory, such as the memory 22 of the programming device 20 (FIG. 2), and may be executed by one or more processors, such as the processor 24 (FIG. 2) of the programming device 20.

The method 100 begins in block 102 when a user activates the programming device 20, such as by directly interacting with the programming device 20 or by remotely operating the programming device 20 via the user control device 40 (FIG. 2). Next, in block 104, the user may design, such as program, at least one temperature and gas sequence for the interior 16 of the incubator 12. Alternatively, in block 106, the user may select at least one preprogrammed (e.g., preset) temperature and gas concentration sequence for the interior 16 of the incubator 12. More specifically, a listing of several preprogrammed temperature and gas concentration sequences, which have been saved to the programming device 20, may be displayed on the display 26 of the programming device 20 upon activation. After being displayed, the user may select one of the preprogrammed temperature and gas concentration sequences for execution within the interior 16 of the incubator 12.

However, if the user designs the temperature and gas concentration sequence (block 104), the user then selects a first temperature T1, a first gas concentration level G1, and a first period of time t1 at which the temperature T1 and the gas concentration G1 will cycle in the interior 16 of the incubator 12 in block 108. The first temperature T1, the first gas concentration level G1, and the first period of time t1 may be selected via the input 28 (FIG. 2) of the programming device 20, for example. In block 110, the user then selects a second temperature T2, a second gas concentration level G2, and a second period of time t2 at which the second temperature T2 and the gas concentration level G2 will cycle in the interior 16 of the incubator 12 after the first time t1 to help effect the dynamic incubation of the stem cells disposed in the incubator 12. In this way, a preprogrammed temperature and gas concentration sequence is designed. In block 112, the preprogrammed temperature and gas concentration sequence is saved to the memory 22 of the programming device 20 and may be listed with other preprogrammed temperature and gas concentration sequences displayed on the display 26 of the programming device 20. Alternatively, the preprogrammed temperature and gas concentration sequence may be listed on the display 18 of the incubator 12 when the programming device 20 is incorporated into the incubator housing 14, as explained above.

In block 114, either the designed or the selected temperature and gas concentration sequence is executed for implementation within the interior 16 of the incubator 12. The temperature and gas concentration sequence includes programmed changes to the temperature and one or more of the $CO_2$ gas concentration or the $O_2$ gas concentration in the interior 16 of the incubator 12 after designated periods of time, such as times t1 and t2.

In block 116, the purging mechanism 60, such as the air pump, purges (e.g., releases) an amount or a portion of gas concentration within the interior 16 of the incubator 12 for period of time tp. In this way, rapid changes in the temperature and gas concentration within the interior 16 of the incubator 12 are able to be effected, contributing to the dynamic incubation of the stem cells. In another example, when the purging mechanism 60 is the water pump 60a, the water pump 60a purges, e.g., cycles and/or releases, an amount of water in one of the internal water pump 65 of the incubator 12 or the water jacket 69 surrounding at least a portion of the interior 16 to the external water tank 67 for a period of time tp. In this way, rapid changes in the temperature within the interior 16 of the incubator 12 are again able to be effected, also contributing to the dynamic incubation of the stem cells.

In one example, executing the at least one temperature and gas concentration sequence for the interior 16 of the incubator 12 of block 114 comprises implementing the selected preprogrammed temperature and gas concentration sequence. This includes setting the first temperature T1 and the first $CO_2$ gas concentration G1 and maintaining the first temperature T1 and the first $CO_2$ gas concentration G1 for a time t1. The executing next includes setting the second temperature T2 and the second $CO_2$ gas concentration G2 and purging a portion of the gas concentration of the interior 16 of the incubator 12 via the purging mechanism 60 for a time tp. The executing step then also includes maintaining the second temperature T2 and the second $CO_2$ gas concentration G2 for a time t2.

In one example temperature and gas concentration sequence, setting the first temperature T1 and the first $CO_2$ gas concentration G1 of the interior 16 of the incubator 12 is setting at the first temperature T1 to 37 degrees C. and the first $CO_2$ gas concentration G1 to 5% $CO_2$. In addition, maintaining the first temperature T1 and the $CO_2$ gas concentration G1 for a time t1 includes for the time t1 of about 8 hours. Further, setting the second temperature T2 and the second $CO_2$ gas concentration to a value G2 includes setting the second temperature 38 degrees C. and the second $CO_2$ gas concentration G2 to 5.5% $CO_2$. Still further, purging a portion of the gas concentration of the interior 16 of the incubator 12 via the purging mechanism 60 for a time tp, or purging an amount of water in one of the internal water pump 65 of the incubator 12 or the water jacket 69 for a time tp, includes for a time of about 1 minute. Lastly, maintaining the second temperature T2 and the second $CO_2$ gas concentration G2 for a time t2 includes for a time t2 of about 30 minutes.

In another example temperature and gas concentration sequence, setting the first temperature T1 and the first $CO_2$ gas concentration G1 includes setting the first temperature T1 to 38 degrees C. and the first $CO_2$ gas concentration G1 to 6% $CO_2$. In addition, maintaining the first temperature T1 and the $CO_2$ gas concentration G1 for a time t1 is for a time t1 of about 60 minutes. Further, setting the second temperature T2 and the second $CO_2$ gas concentration to a value G2 includes setting a second temperature to 37 degrees C. and the second $CO_2$ gas concentration G2 to 5% $CO_2$. Still further, purging the portion of the gas concentration of the interior 16 of the incubator 12 via the purging mechanism 60 for a time tp, or purging an amount of water in one of the internal water pump 65 of the incubator 12 or the water jacket 69 for a time tp, includes for a time of about 1 minute. Lastly, maintaining the second temperature T2 and the second $CO_2$ gas concentration G2 for a time t2 includes for a time t2 of about 8 hours.

In still another example temperature and gas concentration sequence, setting the first temperature T1 and the first $CO_2$ gas concentration G1 includes setting at the first temperature T1 to 36 degrees C. and the first $CO_2$ gas concentration G1 to 5.5% $CO_2$. In addition, maintaining the first temperature T1 and the $CO_2$ gas concentration G1 for a time t1 is for a time t1 of about 120 minutes. Further, setting the second temperature T2 and the second $CO_2$ gas concentration to a value G2 includes setting the second temperature to 37 degrees C. and the second $CO_2$ gas concentration G2 to 5% $CO_2$. Still further, purging a portion of the gas concentration of the interior 16 of the incubator 12 via the purging mechanism 60 for a time tp, or purging an amount of water in one of the internal water pump 65 of the incubator 12 or the water jacket 69 for a time tp, includes for a time of about 1 minute. Lastly, maintaining the second temperature T2 and the second $CO_2$ gas concentration G2 for a time t2 includes for a time t2 of about 20 hours.

In this example, executing at least one temperature and gas concentration sequence via the programming device 20 may further comprise setting an $O_2$ gas concentration level to a value G3 after setting the temperature T1 and the $CO_2$ gas concentration value G1 via the programming device 20. In addition, executing may also include maintaining each of the temperature T1, the $CO_2$ gas concentration value G1, and the $O_2$ gas concentration value G3 for the time t1 via the programming device 20 and setting the $CO_2$ gas concentration value to a value G4 via the programming device 20. Further, executing may include setting the $O_2$ gas concentration value to a value G5 via the programming device 20, and maintaining the $CO_2$ gas concentration value to a value G4 and the $O_2$ gas concentration value to a value G5 for a period of time t1 via the programming device.

In this further example, executing may also include setting the $O_2$ gas concentration value to zero before operating the purging mechanism 60 for a time tp via the programming device 20. In addition, at least one or more of the $O_2$ gas concentration value G3 is 18% $O_2$, the $CO_2$ gas concentration value G4 is 6% $CO_2$, and the $O_2$ gas concentration value G5 is 15% $O_2$.

While various temperature and gas sequences are described above, it will be appreciated that several other temperature and gas sequences having other selected first and second temperatures, first and second gas concentrations, and cycling times may alternatively be used to affect the dynamic incubation results and still fall within the scope of the present disclosure.

Figure 6:
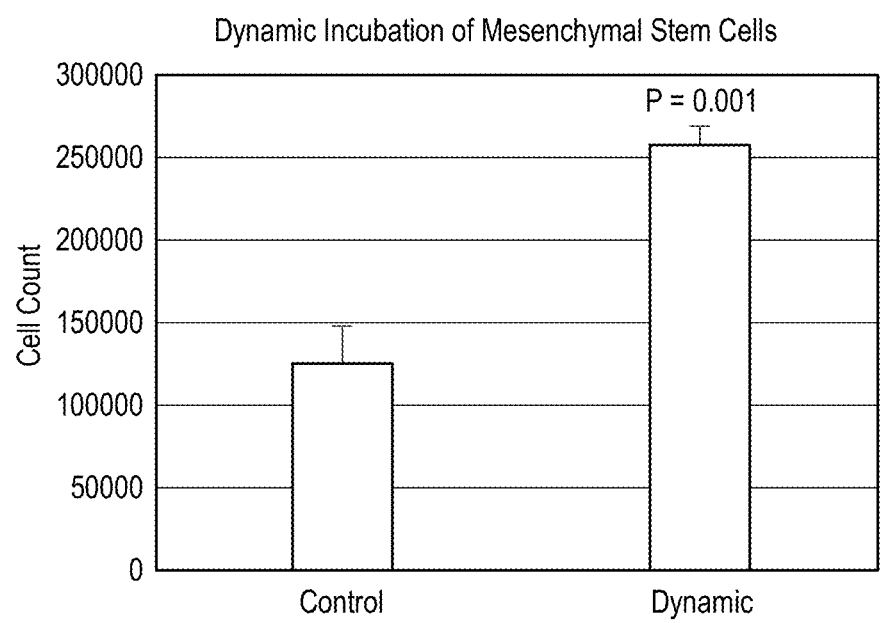
FIG. 6 is a graph depicting the results of a cell proliferation experiment using the dynamic incubator system of the present disclosure.

Referring now to FIG. 6, a graph illustrating the results of a cell proliferation experiment using the dynamic incubator system 10 of the present disclosure is depicted. In this experiment, cell counts of mesenchymal stem cells after 144 hours of culture in controlled temperature and gas concentration (constant 37° C. and 5% $CO_2$) are compared with dynamic incubation using the dynamic incubator system 10 (cycling 37° C. and 5% $CO_2$ for 8 hrs., then 38° C. and 5.5% $CO_2$ for 30 min.). In the experiment, 35,000 human adipose MSCs were plated in a T75 flask, containing 10 mL of α-MEM medium. The P-value is from t-test compared to control.

Figure 7:
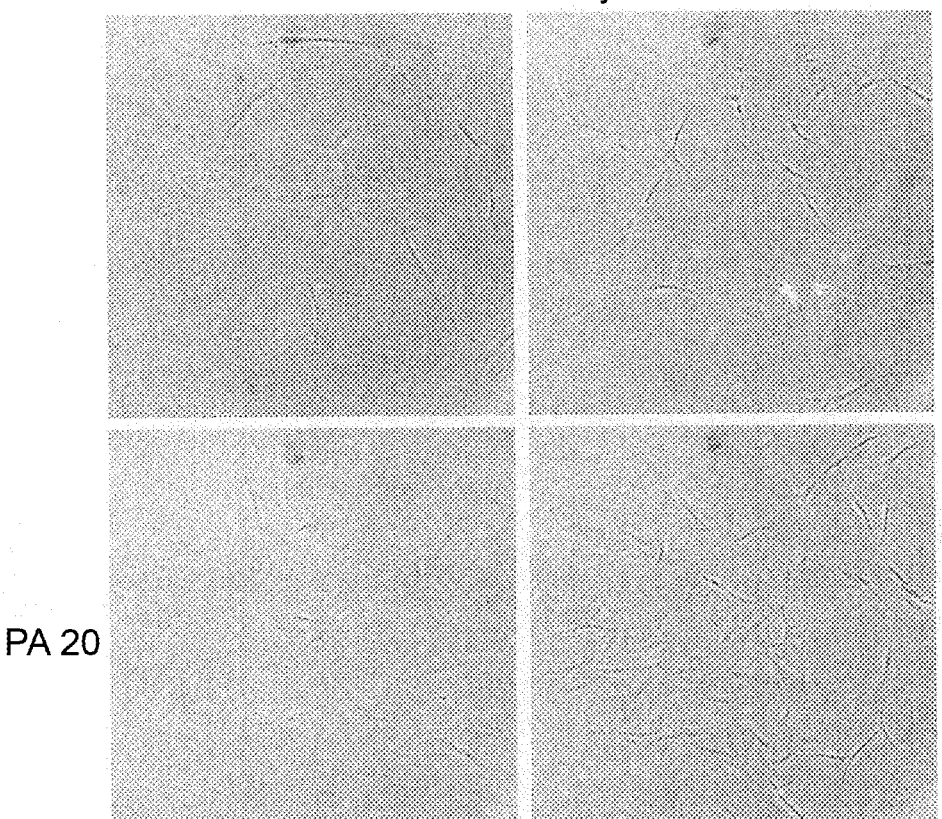
FIG. 7 is a series of photographs depicting the results of a cell morphology experiment involving the dynamic incubator system and methods of the present disclosure.

Referring now to FIG. 7, a series of photographs illustrating the results of a cell morphology experiment involving the dynamic incubator system 10 and methods of the present disclosure is depicted. In this experiment, adipose mesenchymal stem cells after 168 hours of culture in controlled, constant temperature and gas concentration (constant 37° C. and 5% $CO_2$), are compared to dynamic incubation using the dynamic incubator system 10 (cycling 37° C. and 5% $CO_2$ for 8 hrs., then 38° C. and 5.5% $CO_2$ for 30 min.). The experiment was conducted with the presence of an investigational compound (PA20) that reduces MSC senescence. In the experiment, 10,000 human adipose MSCs were plated in a T25 flask, containing 10 mL of α-MEM medium, with 5 uM PA20. The results show that MSCs in dynamic incubation have polar morphology, indicative of a non-differentiated/non-senescent state. The dynamic incubation appeared to have synergistic effect with PA20.

Figure 8:
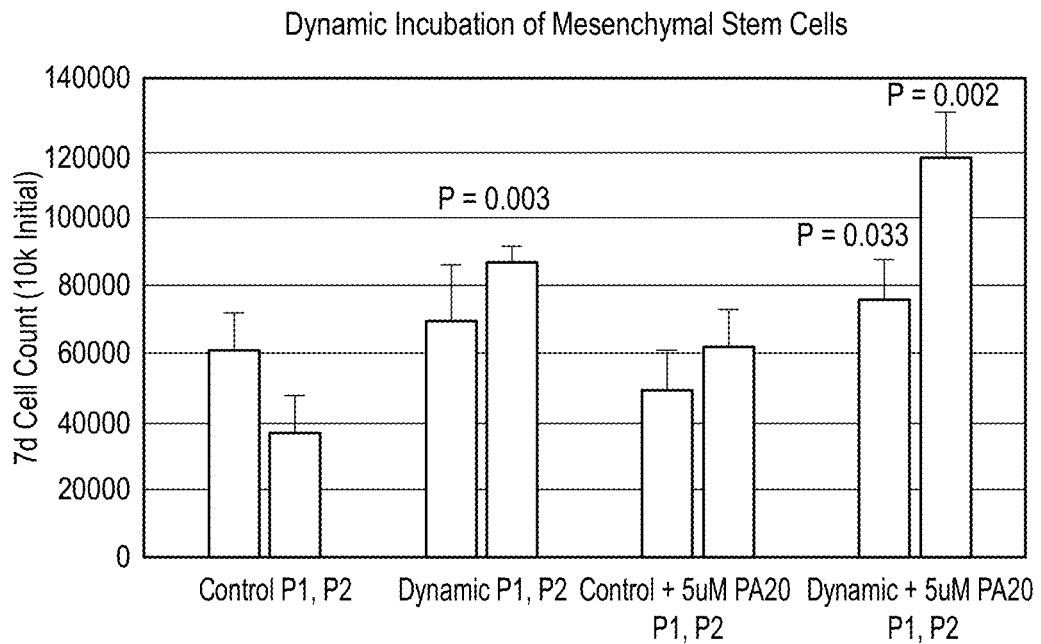
FIG. 8 is another graph depicting the results of another cell proliferation experiment using the dynamic incubator system and methods of the present disclosure.

Referring to FIG. 8, another graph illustrating the results of another cell proliferation experiment using the dynamic incubator system 20 and methods of the present disclosure is depicted. In this experiment, adipose mesenchymal stem cells (A-MSCs) after 168 hours (P1) and an additional 336 hours (P2) of culture in controlled temperature and gas concentration (constant 37° C. and 5% $CO_2$), are compared to dynamic incubation using the dynamic incubator system 10 (cycling 37° C. and 5% $CO_2$ for 8 hrs., then 38° C. and 5.5% $CO_2$ for 30 min.). The experiment included an investigational compound (PA20) that reduces MSC senescence. For each passage (P1 and P2), 10,000 human adipose MSCs were plated in a T25 flask, containing 10 mL of α-MEM medium, with 5 uM PA20. In addition, cells from P1 were re-plated in P2, and P-values are from t-test compared to respective P1 or P2 control. The results show dynamic incubation increases proliferation of A-MSCs, and further increases proliferation in the presence of PA20.

Figure 9:
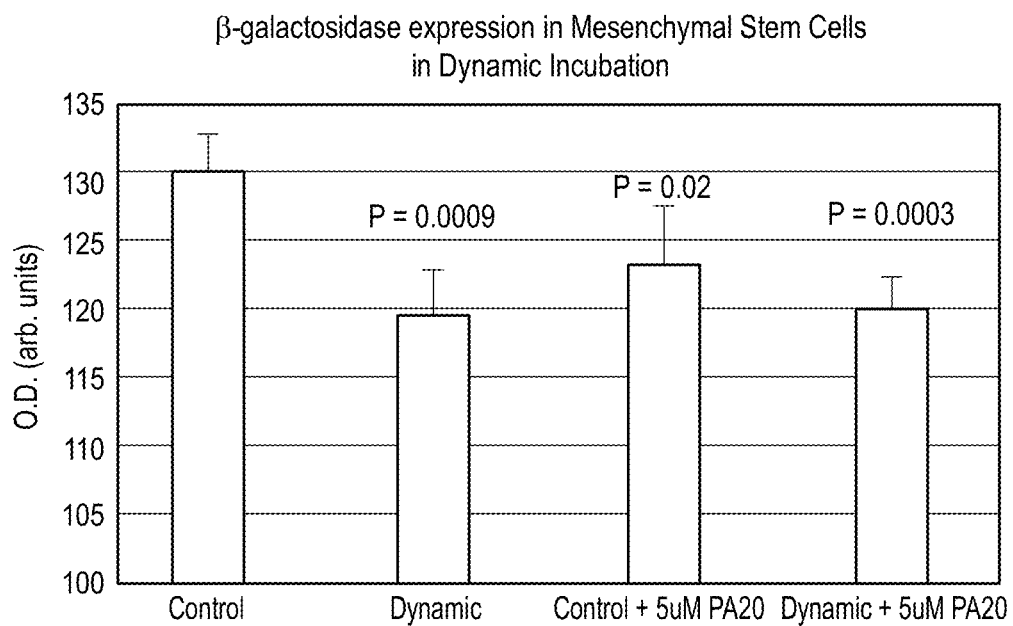
FIG. 9 is a graph depicting the results of a cell senescence experiment using the dynamic incubator system and methods of the present disclosure.

Referring now to FIG. 9, a graph illustrating the results of a cell senescence experiment using the dynamic incubator system 10 and methods of the present disclosure is depicted. In this experiment, adipose mesenchymal stem cells after 168 hours of culture in controlled temperature and gas concentration (constant 37° C. and 5% $CO_2$) are compared with dynamic incubation using the dynamic incubator system 10 (cycling 37° C. and 5% $CO_2$ for 8 hrs., then 38° C. and 5.5% $CO_2$ for 30 min.). The experiment included an investigational compound (PA20) that reduces MSC senescence. In addition, 10,000 human adipose MSCs were plated in a T25 flask, containing 10 mL of α-MEM medium, with 5 uM PA20. β-galactosidase (a marker of cellular senescence) was measured by ELISA assay. Also, p-values are from t-test compared to respective control. The results show that β-galactosidase is reduced by the dynamic incubation.

Figure 10:
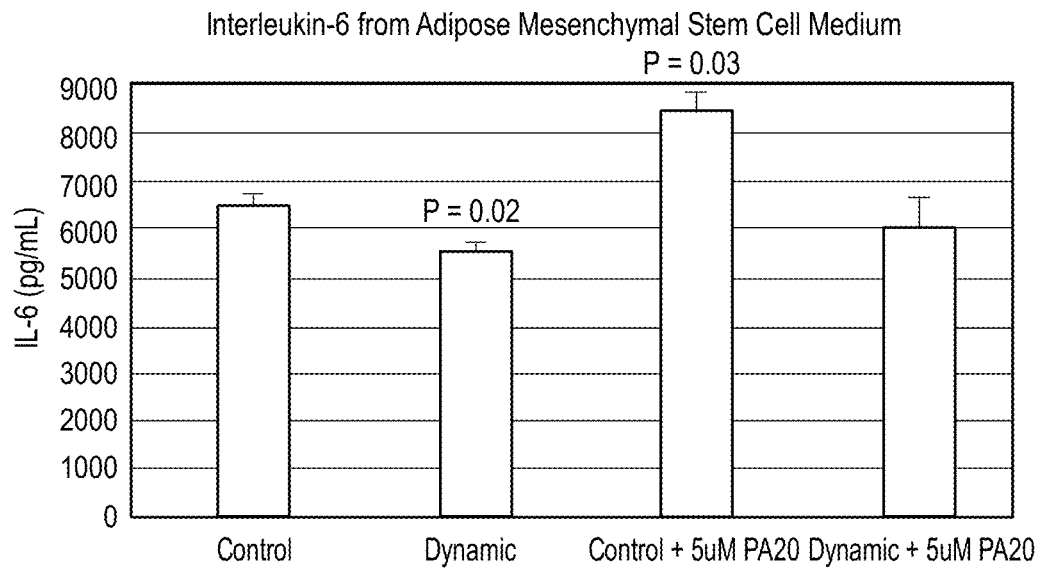
FIG. 10 is another graph depicting the results of an interleukin-6 cell production experiment using the dynamic incubator system and methods of the present disclosure.

Referring now to FIG. 10, another graph illustrating the results of an interleukin-6 (IL-6) cell production experiment using the dynamic incubator system 10 and methods of the present disclosure is depicted. In this experiment, IL-6 is a pro-inflammatory cytokine, and adipose mesenchymal stem cells after 168 hours of culture in controlled temperature and gas concentration (constant 37° C. and 5% $CO_2$) are compared with dynamic incubation using the dynamic incubator system 10 (cycling 37° C. and 5% $CO_2$ for 8 hrs., then 38° C. and 5.5% $CO_2$ for 30 min.). The experiment included the presence of an investigational compound (PA20) that reduces MSC senescence. Further, 10,000 human adipose MSCs were plated in a T25 flask, containing 10 mL of α-MEM medium, with 5 uM PA20. The IL-6 was measured by ELISA assay. The results show that IL-6 is reduced by dynamic incubation. Notably, dynamic incubation reduced PA20-associated increase in IL-6. This indicates that dynamic incubation reversed the agonist effect of PA20 on MSC IL-6 production. In this experiment, p-values are from t-test compared to respective P1 or P2 Control.

Figure 11:
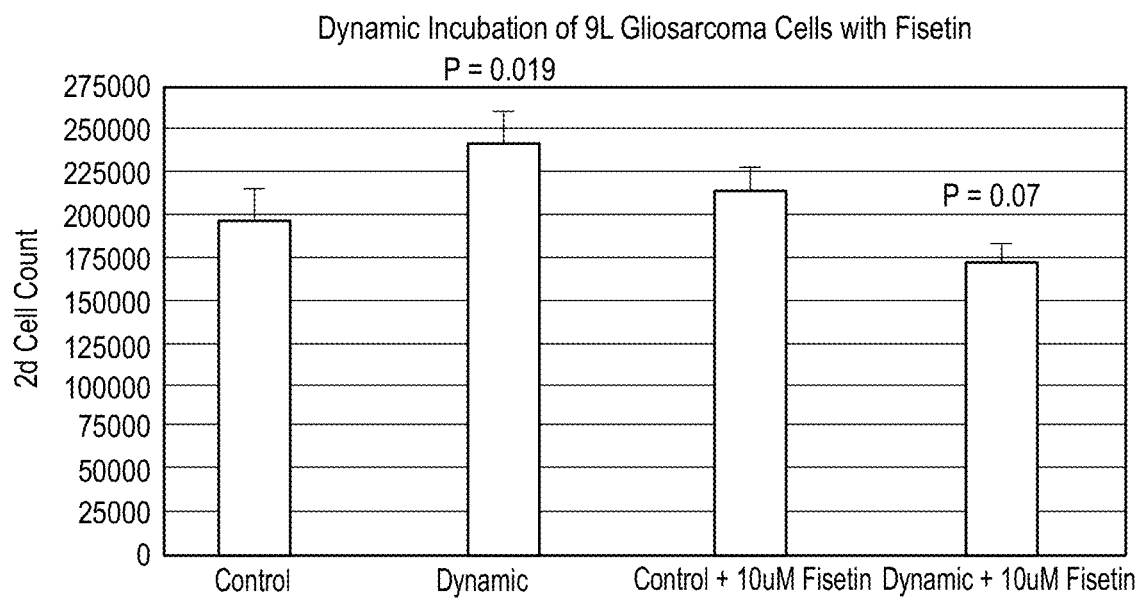
FIG. 11 is another graph illustrating the results of another cell proliferation experiment using the dynamic incubator system and methods of the present disclosure.

Referring now to FIG. 11, another graph illustrating the results of another cell proliferation experiment is depicted. In this experiment, rat 9 L gliosarcoma cells after 72 hours of culture in controlled temperature and gas concentration (constant 37° C. and 5% $CO_2$) are compared with dynamic incubation using the dynamic incubator system 10 (cycling 37° C. and 5% $CO_2$ for 8 hrs., then 38° C. and 5.5% $CO_2$ for 30 min.). The experiment included 10 uM Fisetin. In addition, 100,000 9 L cells were plated in a T75 flask, containing 10 mL of α-MEM medium, with 10 uM Fisetin. In addition, the medium was refreshed after 24 hours without Fisetin, and the cells were then cultured for a 48 additional hours. The results show that the dynamic incubation increases proliferation of 9 L cells, and decreases cell numbers in the presence of Fisetin. P-values are from t-test compared to control.

In view of the foregoing, one of ordinary skill in the art will appreciate the following advantages of the system 10 and methods 100 of the present disclosure described above. For example, and as the foregoing experimental results show, growing cells, such as mammalian cells, in dynamic temperature and gas concentrations according to specific sequences of temperature and gas concentrations (as described above) results in reduced cell doubling time, reduced cellular senescence, and reduced inflammatory cytokine production when compared to cells grown at constant temperature and gas concentrations. Moreover, when dynamic incubation is used in the presence of an investigatory compound, the dynamic incubator system 10 synergistically increased proliferation and reduced cell senescence, but counteracted the compound's activation of IL-6 (an inflammatory cytokine), as explained above. Still further, the purging mechanism 60 allows for the quick purging of the interior incubator atmosphere. This allows for quick changes in the interior temperature and gas concentration to help effect the dynamic incubation.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Some implementations may be described using the expression "coupled" along with its derivatives. For example, some implementations may be described using the term "coupled" to indicate that two or more elements are in direct physical or electrical contact. The term "coupled," however, may also mean that two or more elements are not in direct contact with each other, but yet still co-operate or interact with each other. The implementations are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

Further, while particular implementations and applications have been illustrated and described, it is to be understood that the disclosed implementations are not limited to the precise construction and components disclosed herein. Various modifications, changes and variations, which will be apparent to those skilled in the art, may be made in the arrangement, operation and details of the method and system disclosed herein without departing from the spirit and scope defined in the appended claims.

I claim:

1. A dynamic incubator system for cells, the dynamic incubator system comprising:
   an incubator having a housing with an interior adapted to contain cells, one of an internal water tank disposed within the housing or a water jacket disposed on an outside area of the housing, and a display;
   a programming device communicatively coupled to the incubator via a communication network, the programming device having a memory, one or more processors, a display, and an input mechanism, the programming device adapted to enable at least one preset temperature and gas concentration sequence to be one or more of designed for the interior of the incubator, saved to the memory of the programming device and/or selected for implementation within the interior of the incubator, the at least one temperature and gas concentration sequence including programmed changes to the temperature and a $CO_2$ gas concentration in the interior of the incubator; and
   a purging mechanism coupled to and/or incorporated within the housing of the incubator and including a water pump having an inlet tube coupled to one of the internal water tank or the water jacket, the purging mechanism communicatively coupled to the programming device and adapted to release a one or more of: (1) a portion of a gas concentration disposed within the interior of the incubator; or (2) an amount of water disposed in the internal water tank of the incubator; or (3) an amount of water disposed in a water jacket configured to be disposed on the incubator to enable rapid changes in the temperature and one or more of gas concentration in the interior of the incubator or the amount of water in the internal tank or the water jacket.

2. The system of claim 1, further comprising a module stored in the memory of the programming device and executable by at least one processor of the programming device to:
   (1) set a temperature T1 of the interior of the incubator;
   (2) set a $CO_2$ gas concentration of the interior of the incubator to a value G1;

(3) maintain the temperature T1 and the $CO_2$ gas concentration at the value G1 for a time t1;

(4) set a temperature T2 of the interior of the incubator;

(5) set a $CO_2$ gas concentration of the interior of the incubator to a value G2;

(6) operate the purging mechanism for a time tp to purge a portion of the gas concentration of the interior of the incubator; and (7) maintain the temperature T2 and $CO_2$ gas concentration at the value G2 for a time t2.

3. The system of claim 2, wherein the temperature T1 is 37 degrees C., the $CO_2$ gas concentration value G1 is 5% $CO_2$, the time t1 is about 8 hours, the temperature T2 is 38 degrees C., the $CO_2$ gas concentration value G2 is 5.5% $CO_2$, the time tp is about 1 minute, and the time t2 is about 30 minutes.

4. The system of claim 2, wherein the temperature T1 is 38 degrees C., the $CO_2$ gas concentration value G1 is 6% $CO_2$, the time t1 is about 60 minutes, the temperature T2 is 37 degrees C., the $CO_2$ gas concentration value G2 is 5% $CO_2$, the time tp is about 1 minute, and the time t2 is about 8 hours.

5. The system of claim 2, wherein the temperature T1 is 36 degrees C., the $CO_2$ gas concentration value G1 is 5.5% $CO_2$, the time t1 is about 120 minutes, the temperature T2 is 37 degrees C., the $CO_2$ gas concentration value G2 is 5% $CO_2$, the time tp is about 1 minute, and the time t2 is about 20 hours.

6. The system of claim 5, the module of the programming device is further executable by the processor to:

(1) set a $O_2$ gas concentration level to a value G3 after the temperature T1 and the $CO_2$ gas concentration value G1 are set;

(2) maintain each of the temperature T1, the $CO_2$ gas concentration value G1, and the $O_2$ gas concentration value G3 for the time t1;

(3) set the $CO_2$ gas concentration value to a value G4;

(4) set the $O_2$ gas concentration value to a value G5; and (5) maintain the $CO_2$ gas concentration value to a value G4 and the $O_2$ gas concentration value to a value G5 for a period of time t1.

7. The system of claim 6, the module of the programming device is further executable by the processor to set the $O_2$ gas concentration value to zero before the purging mechanism is operated for a time tp.

8. The system of claim 6, wherein at least one or more of the $O_2$ gas concentration value G3 is 18% $O_2$, the $CO_2$ gas concentration value G4 is 6% $CO_2$, and the $O_2$ gas concentration value G5 is 15% $O_2$.

9. The system of claim 1, the programming device including one or more of a smart phone, a tablet, or a personal computer or incorporated into the housing of the incubator.

10. The system of claim 1, further comprising a user control device communicatively coupled to at least one of the programming device and the communication network, the user control device having a memory, and one or more processors, the user control device to activate the programming device.

11. The system of claim 1, wherein the communication network is one of a wired network or a wireless network.

12. The system of claim 1, wherein the purging mechanism includes an air pump having an air inlet tube coupled to a port in the housing of the incubator and an air outlet tube coupled to the port in the housing of the incubator, the air outlet tube having an air lock assembly, the purging mechanism adapted to enable rapid changes in the gas concentration of the interior of the incubator and prevent loss of gas concentration of the interior of the incubator when the pump is not operating.

13. The system of claim 1, the system further comprising an external water tank coupled to the incubator, wherein the water pump is adapted to enable rapid changes in the temperature of the interior of the incubator by cycling an amount of water to and/or from the internal water tank to the external water tank coupled to the incubator.

14. The system of claim 1, the system further comprising an external water tank coupled to the incubator, wherein the water pump is adapted to enable rapid changes in the temperature of the interior of the incubator by cycling an amount of water to and/or from the water jacket and the external water tank coupled to the incubator.

15. The system of claim 1, the display of the incubator housing listing an actual temperature of the interior of the incubator, an actual gas concentration of the interior of the incubator, and at least one log of a previous actual temperature and an actual gas concentration over a period of time.

* * * * *

UNITED STATES PATENT AND TRADEMARK OFFICE
CERTIFICATE OF CORRECTION

PATENT NO. : 11,667,879 B2
APPLICATION NO. : 16/814696
DATED : June 6, 2023
INVENTOR(S) : Mark Katakowski It is certified that error appears in the above-identified patent and that said Letters Patent is hereby corrected as shown below:

In the Claims

Column 14, Line 4, Claim 8, "02," should be -- $O_2$, --.

Column 14, Line 6, Claim 8, "02." should be -- $O_2$. --.

Signed and Sealed this
Twenty-third Day of April, 2024

Katherine Kelly Vidal
*Director of the United States Patent and Trademark Office*